US008298572B2

(12) United States Patent  (10) Patent No.: US 8,298,572 B2
Iwao et al.  (45) Date of Patent: *Oct. 30, 2012

(54) ADHESIVE PHARMACEUTICAL PREPARATION CONTAINING BISOPROLOL

(75) Inventors: Yoshihiro Iwao, Ibaraki (JP); Katsuyuki Ookubo, Ibaraki (JP); Katsuhiro Okada, Ibaraki (JP); Kunihiro Minami, Fukushima (JP); Shuichiro Yuasa, Fukushima (JP)

(73) Assignees: Nitto Denko Corporation, Osaka (JP); Toa Eiyo Ltd., Tokyo (JP)

( * ) Notice: Subject to any disclaimer, the term of this patent is extended or adjusted under 35 U.S.C. 154(b) by 356 days.

This patent is subject to a terminal disclaimer.

(21) Appl. No.: 12/097,260

(22) PCT Filed: Dec. 13, 2006

(86) PCT No.: PCT/JP2006/324874

§ 371 (c)(1),
(2), (4) Date: Jun. 12, 2008

(87) PCT Pub. No.: WO2007/069661

PCT Pub. Date: Jun. 21, 2007

(65) Prior Publication Data

US 2009/0169604 A1  Jul. 2, 2009

(30) Foreign Application Priority Data

Dec. 13, 2005 (JP) ................ 2005-358470
Dec. 6, 2006 (JP) ................ 2006-328922

(51) Int. Cl.
A61K 9/70 (2006.01)
A61K 47/10 (2006.01)
A61K 47/32 (2006.01)
A61K 31/045 (2006.01)
A61K 31/138 (2006.01)

(52) U.S. Cl. ......... 424/449; 424/448; 514/651; 514/724
(58) Field of Classification Search .................. None
See application file for complete search history.

(56) References Cited

U.S. PATENT DOCUMENTS

| 5,149,719 | A | * | 9/1992 | Ferber et al. ................ 514/772 |
| 6,117,447 | A |   | 9/2000 | Nakano et al. |
| 6,303,141 | B1 |   | 10/2001 | Fischer et al. |
| 6,486,147 | B2 | * | 11/2002 | Baldo et al. ................ 514/178 |
| 7,029,693 | B2 |   | 4/2006 | Hori |
| 7,250,546 | B2 |   | 7/2007 | Tsuruda |
| 2004/0142024 | A1 |   | 7/2004 | Chono et al. |
| 2006/0078604 | A1 | * | 4/2006 | Kanios et al. ................ 424/449 |
| 2009/0012181 | A1 |   | 1/2009 | Amano et al. |
| 2009/0169603 | A1 | * | 7/2009 | Iwao et al. .................. 424/448 |
| 2009/0291126 | A1 | * | 11/2009 | Iwao et al. .................. 424/449 |
| 2010/0098747 | A1 | * | 4/2010 | Iwao et al. .................. 424/449 |
| 2010/0227932 | A1 |   | 9/2010 | Amano et al. |

FOREIGN PATENT DOCUMENTS

| EP | 1 188 436 A2 | 3/2002 |
| EP | 1 652 508 A1 | 5/2006 |
| JP | 03-127727 A | 5/1991 |
| JP | 9-511987 A | 12/1997 |
| JP | 10-152434 A | 6/1998 |
| JP | 11-29496 A | 2/1999 |
| JP | 11-502827 A | 3/1999 |
| JP | 2002-080349 A | 3/2002 |
| JP | 2002-187836 A | 7/2002 |
| JP | 2003-313122 A | 11/2003 |
| JP | 2004-502725 A | 1/2004 |
| JP | 2005-23088 A | 1/2005 |
| JP | 2006-76994 A | 3/2006 |
| JP | 2006225319 A | 8/2006 |
| WO | 01/43729 A1 | 6/2001 |
| WO | 02/03969 A2 | 1/2002 |
| WO | 2005/011662 A1 | 2/2005 |
| WO | 2005/072716 A1 | 8/2005 |
| WO | 2006/080199 A1 | 8/2006 |

OTHER PUBLICATIONS

Tan et al. Pressure-sensitive adhesives for transdermal drug delivery systems. PSTT vol. 2, No. 2, pp. 60-69 (Feb. 1999).*
Office Action issued on Sep. 8, 2011 in the corresponding Chinese Patent Application No. 200680046916.4.
Non-Final Office Action, issued by the US Patent and Trademark Office in related U.S. Appl. No. 12/066,095 on Dec. 15, 2010.
Final Office Action, issued by the US Patent and Trademark Office in related U.S. Appl. No. 12/066,095 on May 20, 2011.
Advisory Action, issued by the US Patent and Trademark Office in related U.S. Appl. No. 12/066,095 on Aug. 25, 2011.
European Patent Office Communication dated Dec. 23, 2008.
VISTANEX PIB General Information (published Nov. 2003).
Extended European Search Report dated Oct. 29, 2008.
Choi, Kor. J. Chem. Eng., 9, 1992.
Communication dated Feb. 29, 2012, issued by the Republic of Colombia Superintendency of Industry and Commerce in Colombian Application No. PCT//08-21712.
Communication dated Feb. 28, 2012, issued by the Japanese Patent Office in Japanese Application No. 2006-235270.
Office Action issued on Feb. 7, 2012, in Taiwanese patent Application No. 095133239.
Office Action issued on Mar. 5, 2012, in Canadian Patent Application No. 2621867.
Office Action issued on Nov. 10, 2011, in Colombian Patent Application No. 0821712.

(Continued)

Primary Examiner — David J Blanchard
Assistant Examiner — Peter Anthopolos
(74) Attorney, Agent, or Firm — Sughrue Mion, PLLC

(57) ABSTRACT

In the adhesive pharmaceutical preparation of the invention containing bisoprolol, a pressure-sensitive adhesive layer is laminated on one side of the backing. The pressure-sensitive adhesive layer contains a branched monoalcohol having from 12 to 28 carbon atoms, a free base of bisoprolol and a polyisobutylene pressure-sensitive adhesive. Accordingly, compatibility of the polyisobutylene pressure-sensitive adhesive with the free base of bisoprolol can be specifically increased. As a result, not only it becomes possible to increase blending amount of the free base of bisoprolol but also bleed of the free base of bisoprolol from the pressure-sensitive adhesive layer can be suppressed and, what is more, the pressure-sensitive adhesion characteristics sufficient from the practical point of view can be obtained.

12 Claims, 1 Drawing Sheet

OTHER PUBLICATIONS

Communication dated Oct. 5, 2011, issued by the Japanese Patent Office in Japanese Application No. 2006-235270.

Extended European Search Report dated Jul. 22, 2011, issued in European application No. 11003489.9.

Communication from the Chinese Patent Office (Decision on Rejection) in CN 200680033186.4 dated May 25, 2011.

Communication from the Mexican Patent Office in MX/a/2008/003328 dated Jun. 2, 2011.

Australian Office Action issued in Application No. 2006288260, dated Nov. 22, 201.

Japanese Information Offer Form dated Apr. 15, 2009.

Japanese Office Action dated Dec. 13, 2011 issued by the Japanese Patent Office in counterpart Japanese Application No. 2006-328922.

Search Report issued Jun. 15, 2012 by the European Patent Office in counterpart European Application No. 06834629.5.

Communication issued Jul. 3, 2012 by the Canadian Intellectual Property Office in counterpart Canadian Application No. 2633125.

Communication issued Jul. 10, 2012 by the Korean Intellectual Property Office in counterpart Korean Application No. Oct. 2008-7005702.

Communication issued Jul. 27, 2012 by the Taiwanese Patent Office in counterpart Taiwanese Application No. 095133239.

* cited by examiner

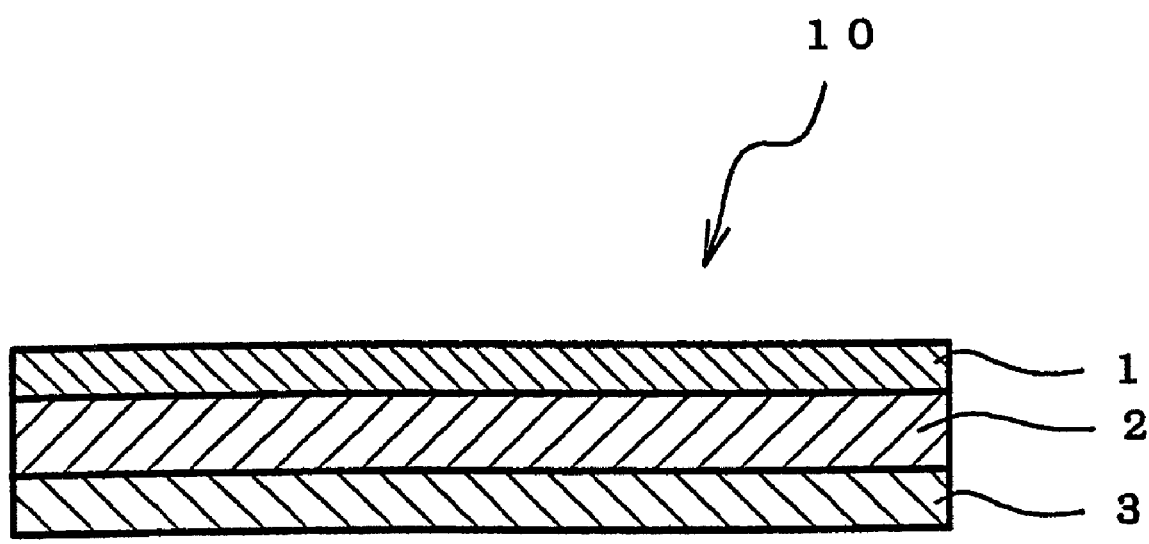

ADHESIVE PHARMACEUTICAL PREPARATION CONTAINING BISOPROLOL

TECHNICAL FIELD

The present invention relates to a percutaneous absorption adhesive pharmaceutical preparation for continuously administering free base of bisoprolol into the body through the skin surface.

BACKGROUND ART

As preparations for carrying out treatment or prevention of diseases by administering a drug into the living body, for example, there are percutaneous absorption pharmaceutical preparations which not only can avoid metabolism of a drug owing to a first pass effect of the liver and various side effects, but also can continuously administer the drug over a prolonged period of time. Among them, development of adhesive pharmaceutical preparations in which a drug is contained in a pressure-sensitive adhesive has been increasingly carried out because of the easy drug application work and the ability to strictly control the dose.

As the basic characteristics required for adhesive pharmaceutical preparations, pressure-sensitive adhesive characteristics may be mentioned from the practical point of view, in addition to the releasing property and stability of the drug. In developing adhesive pharmaceutical preparations, in order to satisfy these basic characteristics, designing of the adhesive pharmaceutical preparations is carried out by selecting most suitable pressure-sensitive adhesive and additive agent in accordance with the drug. As the pressure-sensitive adhesive, an acrylic pressure-sensitive adhesive and a rubber pressure-sensitive adhesive are mainly used, and from the viewpoint of drug stability in the pressure-sensitive adhesive, the rubber pressure-sensitive adhesive which does not have a functional group is generally advantageous than the acrylic pressure-sensitive adhesive. As the rubber pressure-sensitive adhesive, for example, polyisobutylene (PIB) pressure-sensitive adhesive, styrene-isoprene-styrene (SIS) pressure-sensitive adhesive and silicone pressure-sensitive adhesive may be mentioned, but since the SIS and silicone pressure-sensitive adhesives are difficult to be blended with sufficient fatty acid esters which can accelerate absorption of the drug, and the silicone pressure-sensitive adhesive is expensive, blending and selection of these components are limited and, as a result, degree of freedom of the designing of the adhesive pharmaceutical preparation becomes low. Accordingly, as the rubber pressure-sensitive adhesive, polyisobutylene pressure-sensitive adhesive (to be referred sometimes to as "PIB pressure-sensitive adhesive" hereinafter) is easy to use.

However, since the PIB pressure-sensitive adhesive has low polarity, it has a problem of being low in drug solubility. For the purpose of satisfying releasing quantity and persistency of a drug which are required for the adhesive pharmaceutical preparation, although it is desirable to blend the drug in an amount as large as possible, the amount of the drug is limited in the PIB pressure-sensitive adhesive. Even so, in the case of a drug which is solid at room temperature or around room temperature, it is possible to blend the drug in a large amount of its solubility or more by dispersing the solid drug in the pressure-sensitive adhesive. In such a case, since a part of the drug is dispersed in the pressure-sensitive adhesive in the form of crystals and the like, and the concentration of the drug dissolved in the pressure-sensitive adhesive is low, adhesion strength of the pressure-sensitive adhesive itself is not spoiled. That is, when a drug which is solid at room temperature or around room temperature is used, since it becomes possible to attain the blending of the drug in an amount necessary and sufficient for the treatment or prevention as well as the pressure-sensitive adhesive characteristics from the practical point of view, the poor drug solubility of the PIB pressure-sensitive adhesive does not become a large problem.

On the other hand, there are certain drugs which are liquid at room temperature or around room temperature. In the case of such drugs, blending of a drug and pressure-sensitive adhesive characteristics becomes incompatible when a large amount of the drug exceeding its solubility in a pressure-sensitive adhesive is blended in the pressure-sensitive adhesive. That is, a drug which cannot be sufficiently dissolved in a pressure-sensitive adhesive cannot be dispersed and present in the pressure-sensitive adhesive unlike the case of a solid drug, but flows in a PIB pressure-sensitive adhesive during the storage due to the fluidity of the drug itself to thereby exudes on the surface of the pressure-sensitive adhesive layer. This phenomenon of exuding is called bleed, and when the bleed occurs, surface of the pressure-sensitive adhesive layer is covered with the drug to inhibit contact of the pressure-sensitive adhesive with an adherend, so that the adhesion strength of the adhesive pharmaceutical preparation is considerably reduced. In addition, it not only reduce the adhesion strength to an adherend but also causes reduction of adhesiveness of the pressure-sensitive adhesive for the backing, namely reduction of anchorage property.

As the drug which is liquid at room temperature or around room temperature, free base of bisoprolol may be mentioned, but when a large amount of the free base of bisoprolol is blended in a PIB pressure-sensitive adhesive, it causes a problem in that adhesiveness and anchorage property are reduced due to the generation of bleed. Thus, there is a possibility to contain bisoprolol in an adhesive pharmaceutical preparation in the form of a salt such as bisoprolol fumarate, but a drug in a salt form is low in percutaneous absorption ability.

With the aim of improving reduction of pressure-sensitive adhesion characteristics in the case of blending a large amount of a liquid drug in the pressure-sensitive adhesive layer, Patent Reference 1 discloses a percutaneous composition which comprises one or more drugs wherein at least one of them has a low molecular weight and is liquid at room temperature or about room temperature, and a polymer matrix that contains one or more high shearing resistance polymers. It is described that this high shearing resistance polymer reduces the plasticizing effect of the low molecular weight drug and has the tackiness and shearing force sufficient for applying to human. In addition, it is described in its Examples that an acrylic pressure-sensitive adhesive or a blended pressure-sensitive adhesive of an acrylic pressure-sensitive adhesive with a silicone pressure-sensitive adhesive showed a stringiness suppressing effect. Although polyisobutylene is exemplified as the high shearing resistance polymer, the effect thereof is not verified in the Examples and the like, and PIB pressure-sensitive adhesives are not substantially examined.

In addition, according to a view of the present inventors, although it is theoretically possible to suppress stringiness of a pressure-sensitive adhesive in the case of increased blending amount of a liquid drug, by hardening the pressure-sensitive adhesive through the increase of molecular weight of a high shearing resistance polymer, increase of blending ratio of the high shearing resistance polymer and the like as described in the above-mentioned Patent Reference 1, when the pressure-sensitive adhesive is hardened, adhesiveness of the pressure-sensitive adhesive to an adherend is spoiled and adhesion strength of the adhesive pharmaceutical preparation is reduced. Since the acrylic pressure-sensitive adhesive has an originally high level of adhesion strength, reduction of the adhesion strength does not become a serious problem even when it contains a liquid drug, but in the case of the PIB pressure-sensitive adhesive which has low adhesion strength in comparison with the acrylic pressure-sensitive adhesive, when the PIB pressure-sensitive adhesive is hardened, its adhesion strength is sharply reduced so that assuring of its adhesion strength from the practical point of view becomes difficult. Accordingly, it is difficult to apply the method described in the Patent Reference 1 to the polyisobutylene pressure-sensitive adhesive, and it is the actual circumstances that an adhesive pharmaceutical preparation having sufficient pressure-sensitive adhesion characteristics owing to the combination of the free base of bisoprolol and the PIB pressure-sensitive adhesive, has not been obtained yet.

Patent Reference 1: JP-A-2005-23088

DISCLOSURE OF THE INVENTION

The present invention has been made with taking such actual circumstances into consideration, and the problem to be solved in the invention is, in developing an adhesive pharmaceutical preparation for percutaneously administering the free base of bisoprolol into the living body, to provide an adhesive pharmaceutical preparation containing a polyisobutylene pressure-sensitive adhesive as the pressure-sensitive adhesive, which can suppress the bleed of the free base of bisoprolol and has sufficient pressure-sensitive adhesion characteristics.

With the aim of solving the above-mentioned problems, the present inventors have conducted intensive studies and found as a result that, when a specified alcohol is contained in a pressure-sensitive adhesive layer containing a PIB pressure-sensitive adhesive and a free base of bisoprolol, compatibility of the polyisobutylene pressure-sensitive adhesive with the free base of bisoprolol is specifically increased, the bleed can be suppressed as a result and, furthermore, sufficient pressure-sensitive adhesion characteristics can be obtained, thereby resulting in the accomplishment of the invention.

That is, the invention has the following characteristics.

(1) An adhesive pharmaceutical preparation containing bisoprolol, which comprises:
a backing; and
a pressure-sensitive adhesive layer laminated on one side of the backing, said pressure-sensitive adhesive layer containing a branched monoalcohol having from 12 to 28 carbon atoms, a free base of bisoprolol and a polyisobutylene pressure-sensitive adhesive.

(2) The adhesive pharmaceutical preparation containing bisoprolol according to (1) above, wherein the branched monoalcohol is a primary alcohol.

(3) The adhesive pharmaceutical preparation containing bisoprolol according to (1) or (2) above, wherein the branched monoalcohol is a 2-alkyl-1-alkanol.

(4) The adhesive pharmaceutical preparation containing bisoprolol according to (3) above, wherein the number of carbons of the alkyl group at the 2-position of the 2-alkyl-1-alkanol is 2 or more.

(5) The adhesive pharmaceutical preparation containing bisoprolol according to any one of (1) to (4) above, wherein the branched monoalcohol is at least one kind selected from 2-hexyl-1-decanol, 2-octyl-1-decanol, 2-hexyl-1-dodecanol, 2-octyl-1-dodecanol and 2-decyl-1-tetradecanol.

According to the adhesive pharmaceutical preparation of the invention, the compatibility of a polyisobutylene pressure-sensitive adhesive with a free base of bisoprolol can be specifically increased by containing a branched monoalcohol having from 12 to 28 carbon atoms as a solubilizing agent in the pressure-sensitive adhesive layer. As a result, not only it becomes possible to increase blending amount of bisoprolol but also bleed of bisoprolol from the pressure-sensitive adhesive layer can be suppressed and, what is more, the pressure-sensitive adhesion characteristics sufficient from the practical point of view can be obtained. Accordingly, an adhesive pharmaceutical preparation which can achieve compatibility of the pharmacological action with pressure-sensitive adhesion characteristics at high level can be provided.

BRIEF DESCRIPTION OF THE DRAWINGS

FIG. 1 is a sectional view showing an embodiment of the adhesive pharmaceutical preparation of the invention containing bisoprolol.

| Description of the Reference Numerals | |
|---|---|
| 1 | Backing |
| 2 | Pressure-sensitive adhesive layer |
| 3 | Release liner |
| 10 | Adhesive pharmaceutical preparation |

BEST MODE FOR CARRYING OUT THE INVENTION

The following describes the invention in detail based on its suitable embodiments. In this connection, in the description of the drawing, overlapping descriptions are omitted by attaching the same reference numeral to the same element. In addition, for the sake of convenience of the illustration, dimensional ratios of the drawing do not necessarily coincide with the descriptions.

FIG. 1 is a sectional view showing a suitable embodiment of the adhesive pharmaceutical preparation of the invention. The adhesive pharmaceutical preparation 10 is provided with a backing 1, an pressure-sensitive adhesive layer 2 laminated on one side of the backing 1, and a release liner 3 laminated on the pressure-sensitive adhesive layer 2. The pressure-sensitive adhesive layer 2 contains a branched monoalcohol having from 12 to 28 carbon atoms, a polyisobutylene pressure-sensitive adhesive and a free base of bisoprolol.

The branched monoalcohol to be contained in the pressure-sensitive adhesive layer functions as a solubilizing agent in the combination of the free base of bisoprolol which is liquid at 40° C. with a PIB pressure-sensitive adhesive. Furthermore, surprisingly, only the branched monoalcohol having from 12 to 28 (preferably from 16 to 24) carbon atoms can specifically improve the compatibility of the PIB pressure-sensitive adhesive with the free base of bisoprolol. As a result, not only it becomes possible to suppress the bleed of the free base of bisoprolol but also the pressure-sensitive adhesion characteristics sufficient from a practical point of view can be ensured. In this connection, the branched monoalcohol can be used as one species alone or in combination of two or more species. In addition, the number of carbons means the total number of carbons of the carbon skeleton constituting the alcohol.

In order to improve compatibility of the drug with the PIB pressure-sensitive adhesive, it is considered that the compatibility can be improved to a certain degree when a solubilizing agent having a polarity between the drug and the PIB pressure-sensitive adhesive is used. Accordingly, it is considered that two or more compounds (such as esters and acids) other than the above-mentioned alcohol can be used, because their influence upon the compatibility is small even when the number of carbons, the kind or number of polar group or the binding position of polar group is slightly different in comparison with the above-mentioned alcohol. However, even when a fatty acid ester, a diester, an organic acid or the like having the same number of carbons and similar polarity is used instead of the above-mentioned alcohol, strangely, the effect of suppressing the bleed of the free base of bisoprolol cannot be obtained at all or is very small even when it is obtained. In addition, in the case of a monoalcohol which has the same number of carbons and its carbon skeleton is linear chain, since its bulk height is low in comparison with the above-mentioned branched alcohol, intermolecular interaction of the alcohol becomes strong to thereby lower the fluidity of the alcohol itself in some cases. Thus, the fluidity and deformability of the pressure-sensitive adhesive are reduced and adhesion strength of the pressure-sensitive adhesive is also lowered in some cases. In addition, even in the case of a branched monoalcohol, when the number of carbons is smaller than 12, the hydrophobicity based on the carbon nucleus becomes small and the compatibility of free base of bisoprolol with the PIB pressure-sensitive adhesive is rapidly reduced. On the other hand, when the number of carbons is larger than 28, the hydrophobicity becomes so large that the compatibility of free base of bisoprolol with the PIB pressure-sensitive adhesive is reduced.

In describing further illustratively, as the branched monoalcohol having from 12 to 28 carbon atoms, a primary alcohol is desirable because it is apt to interact with the drug due to the aptness of its hydroxyl group to be exposed to the surface of the alcohol molecule and, as a result, solubility of the free base of bisoprolol is significantly improved. Particularly, 2-alkyl-1-alkanol having an excellent balance between its hydroxyl group and carbon skeleton is more preferable. The alcohol has such a structure that one carbon chain branching base point is present and two long carbon chains and one short carbon chain elongate from the base point, in which a hydroxyl group is linked to the tip of the short carbon chain. Owing to the possession of such a structure, the whole alcohol molecules become high in bulk and intermolecular interaction between alcohol molecules is weakened so that fluidity of the alcohol molecules is increased. In addition, since the two long carbon chains efficiently interact as a hydrophobic moiety with the PIB molecule, compatibility of the alcohol molecule with the PIB molecule is improved. Further, since the hydroxyl group of the alcohol molecule does not hide in the inner part of the alcohol molecule but is modestly exposed to the surface of the alcohol molecule, the hydroxyl group can interact with the drug, whereby the compatibility of the alcohol with the free base of bisoprolol is improved. The branching effect of carbon chains of the alcohol molecule and the effect of exposure of hydroxyl group were revealed from the comparison of 2-hexyl-1-decanol with hexadecane-8-ol, as monoalcohols having similar molecular structures (cf. Inventive Example 2 and Comparative Example 6).

As the above-mentioned alcohol, those in which the number of carbons of the alkyl group at the 2-position is 2 or more (preferably from 4 to 12, more preferably from 6 to 10) are particularly suitably used. Illustratively, 2-butyl-1-octanol, 2-ethyl-1-decanol, 2-propyl-1-decanol, 2-hexyl-1-octanol, 2-hexyl-1-decanol, 5,7,7-trimethyl-2-(1,3,3-trimethylbutyl)-1-octanol, 2-heptyl-1-undecanol, 2-ethyl-1-hexadecanol, 2-hexyl-1-dodecanol, 2-octyl-1-decanol, 2-octyl-1-dodecanol, 2-decyl-1-tetradecanol and 2-dodecyl-1-hexadecanol can be exemplified. Among them, 2-octyl-1-dodecanol, 2-hexyl-1-decanol, 2-octyl-1-decanol, 2-hexyl-1-dodecanol and 2-decyl-1-tetradecanol are more preferable.

The content of the above-mentioned alcohol based on the total weight of the pressure-sensitive adhesive layer can be optionally selected depending on the content of free base of bisoprolol and the like and therefore is not particularly limited, but it is generally from 0.1 to 40% by weight, preferably from 0.5 to 35% by weight, more preferably from 0.5 to 30% by weight, most preferably from 0.5 to 25% by weight When the content is smaller than 0.1% by weight, it causes a tendency that the above-mentioned effect cannot be fully obtained while, when the content is larger than 40% by weight, it causes a tendency that the cohesive force and adhesion strength of the whole pressure-sensitive adhesive layer are reduced. The invention can be advantageously carried out when the above-mentioned alcohol content is from 0.1 to 40% by weight, from the viewpoint that the drug bleed can be efficiently suppressed in comparison with the case of using other organic liquid components such as a fatty acid alkyl ester.

The drug to be contained in the pressure-sensitive adhesive layer is the free base of bisoprolol represented by the following formula (1), and the free base of bisoprolol may be blended as it is, or a salt of bisoprolol may be converted into free base by subjecting it to a desalt treatment at the time of the blending or after making the adhesive pharmaceutical preparation. That is, it is sufficient when the free base of bisoprolol is contained in the pressure-sensitive adhesive layer at the time of using the adhesive pharmaceutical preparation.

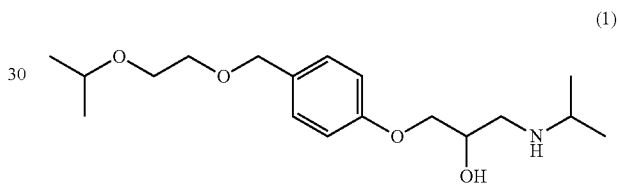

(1)

The content of free base of bisoprolol is not particularly limited and can be optionally selected based on the releasing ability and solubility of the drug and the above-mentioned effect which is obtained depending on the kind and addition amount of the alcohol. The content of free base of bisoprolol based on the total weight of the pressure-sensitive adhesive layer is preferably from 0.5 to 10% by weight, more preferably from 0.5 to 8% by weight, further preferably from 0.5 to 6% by weight. When the content of free base of bisoprolol is less than 0.5% by weight, its bleeding can be suppressed owing to the sufficiently low concentration of the free base of bisoprolol, but there is a tendency that the effect owing to the addition of the above-mentioned alcohol cannot be sufficiently expressed. On the other hand, when the content of free base of bisoprolol exceeds 10% by weight, since the concentration of the free base of bisoprolol is too high, there is a tendency that the bleed suppressing effect owing to the addition of the above-mentioned alcohol cannot be sufficiently expressed. When the content of free base of bisoprolol is from 0.5 to 10% by weight, a remarkable difference in the bleed suppressing effect is recognized depending on the presence or absence of the addition of the above-mentioned alcohol, so that the invention has a technically large significance from this point of view.

In addition, the PIB pressure-sensitive adhesive to be used in the adhesive pharmaceutical preparation of the invention is not particularly limited so long as it essentially contains polyisobutylene and it has appropriate tackiness and cohesiveness as the pressure-sensitive adhesive by itself, and one species alone or a combination of two or more species may be used. In addition, when polyisobutylene is contained in one species alone, molecular weight of the polyisobutylene is not particularly limited, but its viscosity average molecular weight is preferably from 40,000 to 5,500,000, more preferably from 45,000 to 5,000,000. When the viscosity average molecular weight is less than 40,000, there is a possibility that it becomes difficult to provide internal cohesive force necessary for the pressure-sensitive adhesive layer while, when it exceeds 5,500,000, there is a possibility that skin adhesiveness and tack of the pressure-sensitive adhesive layer are deteriorated.

From the viewpoint of easily achieving appropriate flexibility of the pressure-sensitive adhesive layer as well as its irritation to the skin, it is desirable to contain at least two species of polyisobutylene. As such polyisobutylene, those which are constituted of a combination of a first polyisobutylene and a second polyisobutylene having a lower molecular weight than that of the first polyisobutylene is preferable. In this connection, it is needless to say that other polyisobutylene having a different molecular weight can be combined in addition to the first and second polyisobutylene. In this case, the "at least two species of polyisobutylene having different molecular weights" according to the present specification means a polyisobutylene which has molecular weight distribution peaks measured by a gel permeation chromatography (GPC) in at least two independent areas.

When the polyisobutylene is constituted of two species of polyisobutylene, molecular weight of each polyisobutylene is not particularly limited, but it is desirable for obtaining excellent tackiness that the viscosity average molecular weight of the first polyisobutylene is preferably from 1,800,000 to 5,500,000, more preferably from 2,000,000 to 5,000,000, and the viscosity average molecular weight of the second polyisobutylene is preferably from 40,000 to 85,000, more preferably from 45,000 to 65,000. In this case, when the viscosity average molecular weight of the first polyisobutylene is less than 1,800,000, there is a tendency that it becomes difficult to obtain the internal cohesive force necessary for the pressure-sensitive adhesive layer while, when it exceeds 5,500,000, there is a tendency that skin adhesiveness and tack of the pressure-sensitive adhesive layer are reduced. In addition, when the viscosity average molecular weight of the second polyisobutylene is less than 40,000, there is a possibility that a sticky feeling is expressed in the pressure-sensitive adhesive layer to thereby stain the skin surface while, when it exceeds 85,000, there is a tendency that skin adhesiveness and tack of the pressure-sensitive adhesive layer are reduced.

In this connection, the viscosity average molecular weight according to the present specification means a value obtained by calculating Staudinger's index ($J_0$) by Suhulz-Blaschke formula from the capillary flow time of Ubbelohde's viscometer at 200° C., and calculating it according to the following formula using this $J_0$ value.

$$J_0 = \eta_{SP}/c(1+0.31\eta_{SP}) \text{cm}^3/\text{g (Suhulz-Blaschke formula)}$$

$$\eta_{SP} = t/t_0 - 1$$

t: flow time of the solution (by Hagenbach-couette correction formula)

$t_0$: flow time of the solvent (by Hagenbach-couette correction formula)

c: concentration of the solution (g/cm$^2$)

$$J_0 = 3.06 \times 10^{-2} Mv^{0.65}$$

Mv: viscosity average molecular weight

When the polyisobutylene is constituted of two species of polyisobutylene having different molecular weights, blending ratio of the first polyisobutylene to the second polyisobutylene in terms of weight ratio is preferably from 1/0.1 to 1/3, more preferably from 1/0.1 to 1/2.5, further preferably from 1/0.3 to 1/2. Of these two species of polyisobutylene, when blending ratio of the second polyisobutylene is less than the lower limit, there is a tendency that reduction of the skin adhesion strength of the pressure-sensitive adhesive layer becomes large while, when it exceeds the above-mentioned upper limit, there is a tendency that reduction of the internal cohesive force of the pressure-sensitive adhesive layer becomes large.

The total polyisobutylene content based on total weight of the pressure-sensitive adhesive layer is preferably from 15 to 70% by weight, more preferably from 15 to 60% by weight. When the polyisobutylene content is less than 15% by weight, there is a possibility that it becomes difficult to provide internal cohesive force necessary for the pressure-sensitive adhesive layer while, when it exceeds 70% by weight, there is a possibility that skin adhesiveness and tack of the pressure-sensitive adhesive layer are reduced.

According to the invention, it is desirable to contain a tackifier in the polyisobutylene pressure-sensitive adhesive for the purpose of adjusting adhesion strength. As the tackifier, those which are conventionally known in the field of adhesive pharmaceutical preparations can be optionally selected and used, and examples thereof include petroleum resins, terpene resins, rosin resins, coumarone-indene resins, styrene resins, and alicyclic saturated hydrocarbon resins. Among them, alicyclic saturated hydrocarbon resins are preferable because of its excellent drug storage stability. In addition, from the viewpoint of obtaining good tack, a tackifier having a softening point of preferably from 90 to 150° C., more preferably from 95 to 145° C., is used. For example, in the case of alicyclic saturated hydrocarbon resins, tack and cohesive force of the pressure-sensitive adhesive layer tend to be lowered when the softening point is less than 90° C. while, when it exceeds 150° C., there is a tendency that the pressure-sensitive adhesive layer becomes hard to thereby deteriorate the skin adhesiveness. Accordingly, the skin adhesiveness, cohesive force and drug stability may be improved when the adhesive pharmaceutical preparation is prepared by optionally selecting the kind and softening point of the tackifier. In this connection, the softening point according to the present specification means a value measured in accordance with the ring and ball method (JIS K 6863).

As the alicyclic saturated hydrocarbon resin, for example, Alcon P-100, Alcon P-115, Alcon P-125 and Alcon P-140 (trade names, mfd. by Arakawa Chemical Industries) may be mentioned as articles on the market.

The tackifier can be used as one species or in combination of two or more species, and when used in combination of two or more species, for example, resins having different kinds and softening points may be combined.

The content of the tackifier based on the total weight of the pressure-sensitive adhesive layer is preferably from 15 to 55% by weight, more preferably from 20 to 50% by weight. When the content of the tackifier is less than 15% by weight, tack is poor in some cases while, when it exceeds 55% by weight, there is a tendency that the pressure-sensitive adhesive layer becomes hard to thereby deteriorate the skin adhesiveness.

In addition, according to the invention, from viewpoint of the absorption acceleration of free base of bisoprolol and the like, an organic liquid component other than the above-mentioned alcohol and free base of bisoprolol may also be optionally contained. The organic liquid component is not particularly limited so long as it is compatible with the polyisobutylene and tackifier, and a fatty acid alkyl ester may for example be mentioned.

Examples of the fatty acid alkyl ester include a fatty acid alkyl ester obtained from a higher fatty acid having from 12 to 16, preferably from 12 to 14 carbon atoms and a lower monoalcohol having from 1 to 4 carbon atoms. The higher fatty acid is preferably lauric acid (C12), myristic acid (C14) or palmitic acid (C16), and more preferably myristic acid. As the lower monoalcohol, methyl alcohol, ethyl alcohol, propyl alcohol, isopropyl alcohol, butyl alcohol and the like may be exemplified, of which isopropyl alcohol is preferred. Accordingly, most preferred fatty acid alkyl ester is isopropyl myristate.

The organic liquid component may be used one species alone or as a combination of two or more species. The content of the organic liquid component based on the total weight of the pressure-sensitive adhesive layer is preferably from 1 to 40% by weight, more preferably from 3 to 35% by weight. When the organic liquid component content is less than 1% by weight, there is a tendency that absorption acceleration and the like effects are not sufficiently exerted while, when it exceeds 40% by weight, there is a tendency that the adhesion strength and cohesive force of the whole pressure-sensitive adhesive are reduced.

The backing is not particularly limited, but those being substantially practically impermeable to drugs is preferably used; that is, the backing causing no decrease of the content because free base of bisoprolol as active ingredient and additives and the likes are lost from the rear side across the backing. As the backing, for example, a single film of polyester, nylon, polyvinylidene chloride, polyethylene, polypropylene, polyvinyl chloride, ethylene-ethyl acrylate copolymer, polytetrafluoroethylene, ionomer resin, metal foil or the like or a laminate film thereof and the like may be used. Among these, in order to further improve adhesiveness (anchorage property) of the backing with the pressure-sensitive adhesive layer, it is also possible to make the backing into a laminate film of a non-porous plastic film of the above-mentioned material and a porous film. In this case, it is desirable to form the pressure-sensitive adhesive layer on the porous film side.

As such a porous film, those which improve anchorage property with the pressure-sensitive adhesive layer are employed, and illustratively, paper, woven fabric, non-woven fabric, knitting, a mechanically punching-treated sheet and the like can be exemplified. Among these, paper, woven fabric and non-woven fabric are particularly preferred from the viewpoint of easiness of handling and the like. A porous film having a thickness of from 10 to 200 μm is employed in view of the improvement of anchorage property, flexibility of the whole adhesive pharmaceutical preparation, and easiness of sticking. In a case of relatively thin adhesive pharmaceutical preparation such as plaster type or adhesive tape type, those which have a thickness of from 10 to 100 μm are employed.

Further, in the case where a woven fabric or a non-woven fabric is used as the porous film, its basis weight is preferably from 5 to 30 g/m$^2$, and more preferably from 6 to 15 g/m$^2$. As the most favorable backing, a laminated film of a polyester film (preferably a polyethylene terephthalate film) having a thickness of from 1.5 to 6 μm and a non-woven fabric made of a polyester (preferably polyethylene terephthalate) having a basis weight of from 6 to 12 g/m$^2$ is exemplified.

In the adhesive pharmaceutical preparation of the invention, for the purpose of protecting the pressure-sensitive adhesive surface of the pressure-sensitive adhesive layer until the time of use, it is desirable that a release liner is laminated on the pressure-sensitive adhesive surface. The release liner is not particularly limited so far as it can be subjected to a releasing treatment and is able to assure a sufficiently light peeling force, and the examples of the release liner include films such as polyesters, polyvinyl chloride, polyvinylidene chloride and polyethylene terephthalate, papers such as high-quality papers and glassine papers or film of polyolefin laminated with high quality paper or glassine paper, to which releasing treatment is made by applying silicone resin or fluororesin on the surface contacting with the pressure-sensitive adhesive layer. The thickness of the release liner is preferably from 10 to 200 μm, and more preferably from 25 to 100 μm.

As the release liner, one made of a polyester (especially polyethylene terephthalate) resin is preferable from the standpoints of barrier properties, costs and the like. Furthermore, in that case, one having a thickness of from about 25 to 100 μm is preferable from the standpoint of easiness of handling.

The adhesive pharmaceutical preparation of the invention can be produced, for example, by dissolving a PIB pressure-sensitive adhesive containing two species of polyisobutylene having different molecular weights and a tackifier, the above-mentioned alcohol and the free base of bisoprolol into an appropriate solvent such as toluene, forming a pressure-sensitive adhesive layer by applying and drying the thus obtained solution of composition for forming the pressure-sensitive adhesive layer on a release liner, and then laminating a backing on the pressure-sensitive adhesive layer. Alternatively, it can also be produced, for example, by directly applying the above-mentioned solution of the composition for forming the pressure-sensitive adhesive layer on a backing and drying it, thereby forming the pressure-sensitive adhesive layer on the backing. It is difficult in some cases to uniformly dry the solution of the composition for forming the pressure-sensitive adhesive layer when this is thickly applied in one portion, so that it is also possible to repeat the applying operation twice or more to give a pressure-sensitive adhesive layer having sufficient thickness. In this connection, thickness of the pressure-sensitive adhesive layer is generally from 10 to 300 μm, preferably from 20 to 250 μm. In addition, shape of the adhesive pharmaceutical preparation is not particularly limited, and for example, it may be a tape shape, a sheet shape or the like.

It is preferable that the adhesive pharmaceutical preparation of the invention is preserved or transported in a form of sealed package just before use. Packaging may be made, for example, by packing a single sheet of adhesive pharmaceutical preparation or several sheets of piled adhesive pharmaceutical preparations with a wrapping material and then tightly closing the periphery with a heat seal. The wrapping material includes, for example, a sheet-form or film-form material, for which there is no particular limitation. In this case, a material allowing heat sealing is desirous in view of easiness of packaging or air-tightness. Such a packaging material includes, specifically and preferably, those using a heat-sealable plastic sheet such as polyethylene, ionomer resin, ethylene-vinyl acetate copolymer, ethylene-vinyl alcohol copolymer, polyacrylonitrile copolymer, polyvinyl alcohol copolymer, and the like. In particular, in order to prevent the contamination or oxidation of an active ingredient bisoprolol contained in the adhesive pharmaceutical preparation by contact with ambient air, it is preferred to use a laminated gas-impermeable film such as polyester film or metal foil. The packaging material is used in thickness of 10 to 200 μm. It is more preferable to use a high barrier polyacrylonitrile copolymer as the most inner layer of the above packaging material.

Further, it is appropriate to think out a packaging form formed by embossing of the packaging material, dry edge processing (slightly enlarging the above liner portion compared to the adhesive pharmaceutical preparation) or blister molding processing (making the contact area small), since it is feared that handling of the package such as taking-out from the package becomes worse when the pressure-sensitive adhesive ingredient is flowed out from the side of the adhesive pharmaceutical preparation.

The adhesive pharmaceutical preparation of the invention may be taken out from the package, for example by tearing the above package, just before use, and the release liner is peeled off, and the exposed pressure-sensitive adhesive surface is then applied to the skin.

In addition, although it varies depending on the age, body weight, symptoms and the like of the patient, the adhesive pharmaceutical preparation of the invention is applied to the skin surface generally about once a day or two days in the case of adult.

EXAMPLES

The following describes the invention further illustratively with reference to examples, but these examples do not limit the invention. In this connection, the abbreviations to be used in the examples and the like are as follows.

PIB-A: PIB pressure-sensitive adhesive (composition: B200/6H/P140=34/26/40)

PIB-B: PIB pressure-sensitive adhesive (composition: B150/B12/P100=30/30/40)

B12: Oppanol® B12 (mfd. by BASF) polyisobutylene, viscosity average molecular weight of 55,000

B150: Oppanol® B150 (mfd. by BASF) polyisobutylene, viscosity average molecular weight of 2,600,000

B200: Oppanol® B200 (mfd. by BASF) polyisobutylene, viscosity average molecular weight of 4,000,000

6H: HIMOL 6H (mfd. by Nippon Petrochemicals) polyisobutylene, viscosity average molecular weight of 60,000

P100: ARKON® P100 (mfd. by Arakawa Chemical Industries) tackifier, alicyclic saturated hydrocarbon resin, softening point of 100° C.

P140: ARKON® P140 (mfd. by Arakawa Chemical Industries) tackifier, alicyclic saturated hydrocarbon resin, softening point of 140° C.

18SP: LISONOL 18SP (mfd. by Kokyu Alcohol Kogyo) a mixture of 2-octyl-1-decanol/2-hexyl-1-dodecanol=1/1

IPM: Isopropyl myristate

IPP: Isopropyl palmitate

Inventive Examples 1 to 8 and Comparative Examples 1 to 8

A viscous solution was prepared by dissolving each composition for forming pressure-sensitive adhesive layer formulated in accordance with Table 1 in toluene. The solution thus obtained was coated on a silicone release treatment-applied liner (75 μm) made of polyethylene terephthalate (PET) to yield a thickness of 80 μm after drying, and a pressure-sensitive adhesive layer was formed by drying the same in a hot air circulation dryer to thereby remove toluene. Subsequently, a PET film having a thickness of 25 μm as a backing was applied on the pressure-sensitive adhesive layer to obtain a sheet-shaped adhesive pharmaceutical preparation.

TABLE 1

Formulation of composition for forming pressure-sensitive adhesive layer

| | Drug (content; wt %) | Solubilizing agent (content; wt %) | Other components (content; wt %) |
|---|---|---|---|
| Inv. Ex. 1 | Free base of bisoprolol (2) | 2-Octyl-1-dodecanol (5) | PIB-A (83) IPM (10) |
| Inv. Ex. 2 | Free base of bisoprolol (2) | 2-Hexyl-1-decanol (5) | PIB-A (83) IPM (10) |
| Inv. Ex. 3 | Free base of bisoprolol (2) | 18SP (5) | PIB-A (83) IPM (10) |
| Inv. Ex. 4 | Free base of bisoprolol (2) | 2-Decyl-1-tetradecanol (5) | PIB-A (83) IPM (10) |
| Inv. Ex. 5 | Free base of bisoprolol (2.5) | 2-Octyl-1-dodecanol (25) | PIB-A (72.5) |
| Inv. Ex. 6 | Free base of bisoprolol (3.5) | 2-Octyl-1-dodecanol (25) | PIB-A (71.5) |
| Inv. Ex. 7 | Free base of bisoprolol (2) | 2-Octyl-1-dodecanol (15) | PIB-B (83) |
| Inv. Ex. 8 | Free base of bisoprolol (2) | 2-Octyl-1-dodecanol (5) | PIB-A (83) IPP (10) |
| Comp. Ex. 1 | Free base of bisoprolol (2) | IPM (15) | PIB-A (83) |
| Comp. Ex. 2 | Free base of bisoprolol (2) | IPP (5) | PIB-A (83) IPM (10) |
| Comp. Ex. 3 | Free base of bisoprolol (2) | Isostearic acid (5) | PIB-A (83) IPM (10) |
| Comp. Ex. 4 | Free base of bisoprolol (2) | Propylene glycol dicaprylate (5) | PIB-A (83) IPM (10) |
| Comp. Ex. 5 | Free base of bisoprolol (2) | Eicosan-1-ol (5) | PIB-A (83) IPM (10) |
| Comp. Ex. 6 | Free base of bisoprolol (2) | Hexadecan-8-ol (5) | PIB-A (83) IPM (10) |
| Comp. Ex. 7 | Free base of bisoprolol (2) | 2-Ethyl-1-hexanol (5) | PIB-A (83) IPM (10) |
| Comp. Ex. 8 | Free base of bisoprolol (5.5) | IPM (25) | PIB-A (69.5) |

The following tests were carried out using the respective adhesive pharmaceutical preparations obtained in Inventive Examples 1 to 8 and Comparative Examples 1 to 8.

1. Bleed Resistance

Whether or not a liquid substance was adhered to the liner when the liner was peeled off from the adhesive pharmaceutical preparation was visually observed and evaluated by the following criteria. The evaluation results are shown in Table 2.

O: A liquid substance was not adhered to the liner.
Δ: A liquid substance was slightly adhered to the liner.
X: A liquid substance was massively adhered to the liner.

2. Bleed Quantity

The liner was peeled off from the adhesive pharmaceutical preparation and the pressure-sensitive adhesive layer adherent side of the liner was washed with methanol, and adhered amount of the free base of bisoprolol was determined by HPLC. In this connection, the adhered amount was determined as its ratio to the free base of bisoprolol blended in the composition for forming pressure-sensitive adhesive layer. The results are shown in Table 2.

3. Anchorage Property

Whether or not the pressure-sensitive adhesive layer was anchored to the backing side when the liner was peeled off from the adhesive pharmaceutical preparation (liner release operation) was evaluated. In addition, whether or not the pressure-sensitive adhesive layer was anchored to the backing side when an adhesive pharmaceutical preparation was applied to a phenol resin plate and the adhesive pharmaceutical preparation was peeled off therefrom was evaluated (adhesiveness test). In this connection, the anchorage property was evaluated based on the following criteria. The evaluation results are shown in Table 2.

O: The pressure-sensitive adhesive layer was anchored to the backing in accordance with both of the liner release operation and adhesiveness test.

Δ: The pressure-sensitive adhesive layer was anchored to the backing in accordance with the liner release operation, but the pressure-sensitive adhesive layer was not anchored to the backing in accordance with the adhesiveness test.

X: The pressure-sensitive adhesive layer was not anchored to the backing in accordance with the liner release operation.

4. Adhesion Feeling

With respect to the adhesion feeling when the pressure-sensitive adhesive layer exposed after peeling of the liner was touched with a finger, sensory evaluation was carried out based on the following criteria. The evaluation results are shown in Table 2.

O: The adhesion feeling was sufficiently strong.
Δ: The adhesion feeling was slightly weak.
X: The adhesion feeling was weak.

5. Adhesion Strength

Adhesion strength (peeling strength) was measured by applying each belt-shaped sample cut into a width of 24 mm to a phenol resin plate, closely adhering it by one reciprocation of a roller having a load of 850 g, and then peeling it off to the 180 degree direction at a rate of 300 mm/minute. The measured results are shown in Table 2.

TABLE 2

|  | Bleed resistance | Bleed quantity (wt %, per blended amount) | Anchorage property | Adhesion feeling | Adhesion strength (N/24 mm) |
|---|---|---|---|---|---|
| Inv. Ex. 1 | O | 0.1 | O | O | 4.4 |
| Inv. Ex. 2 | O | 0.1 | O | O | 5.5 |
| Inv. Ex. 3 | O | 0.1 | O | O | 6.3 |
| Inv. Ex. 4 | O | 0.1 | O | O | 5.0 |
| Inv. Ex. 5 | O | Not measured | O | O | 3.5 |
| Inv. Ex. 6 | O | Not measured | O | O | 3.4 |
| Inv. Ex. 7 | O | Not measured | O | O | 10.7 |
| Inv. Ex. 8 | O | Not measured | O | O | 3.0 |
| Comp. Ex. 1 | X | 2.1 | X | Δ | Not measurable |
| Comp. Ex. 2 | X | 2.1 | X | Δ | Not measurable |
| Comp. Ex. 3 | Δ | 0.6 | X | Δ | Not measurable |
| Comp. Ex. 4 | X | 1.6 | X | X | Not measurable |
| Comp. Ex. 5 | Δ | 0.5 | X | X | Not measurable |
| Comp. Ex. 6 | O | Not measured | O | Δ | 1.9 |
| Comp. Ex. 7 | X | Not measured | X | X | Not measurable |
| Comp. Ex. 8 | X | Not measured | X | X | Not measurable |

(Evaluation Results)

In the adhesive pharmaceutical preparations of Inventive Examples 1 to 4, respectively having a pressure-sensitive adhesive layer to which 2-octyl-1-dodecanol, 2-hexyl-1-decanol, a mixture of 2-octyl-1-decanol/2-hexyl-1-dodecanol=1/1, or 2-decyl-1-tetradecanol was added, bleed was hardly observed, both of their anchorage property and adhesion feeling were good, and the adhesion strength was also sufficient.

On the other hand, in the adhesive pharmaceutical preparations of Comparative Examples 1 to 5 and 7, respectively having a pressure-sensitive adhesive layer to which isopropyl myristate (ester), isopropyl palmitate (ester), isostearic acid (acid), propylene glycol dicaprylate (diester), eicosan-1-ol (straight chain alcohol) or 2-ethyl-1-hexanol (2-alkyl-1-alkanol having 8 carbon atoms) was added, bleed was clearly found, adhesion feeling was weak, anchorage property was insufficient and, what is more, adhesion strength was not measurable because of the insufficient anchorage property for the backing. In this connection, in the case of the adhesive pharmaceutical preparations of Comparative Examples 1 and 2 which did not contain the branched monoalcohol of the invention having from 12 to 28 carbon atoms but contained isopropyl myristate or isopropyl palmitate as the solubilizing agent, the above-mentioned deficiencies were generated, but when used jointly with the branched monoalcohol having from 12 to 28 carbon atoms like the case of the adhesive pharmaceutical preparations of Inventive Examples 1 to 4 and 8, percutaneous absorption accelerating effect and the like desired effects are exerted together with the effects of the invention. In addition, in the adhesive pharmaceutical preparation of Comparative Example 6, having a pressure-sensitive adhesion layer to which hexadecan-8-ol that has a structure similar to 2-hexyl-1-decanol but is a straight chain secondary alcohol was added, although it had anchorage property and its adhesive strength was measurable, its adhesion feeling and adhesion strength were insufficient in comparison with those of Inventive Examples 1 to 4.

In addition, as is evident from the results of Inventive Examples 5 and 6, it became possible to increase blending amount of the free base of bisoprolol by blending 25% by weight of 2-octyl-1-dodecanol. On the other hand, in the case of Comparative Example 8 in which 25% by weight of isopropyl myristate (ester) was blended, when 5.5% by weight of the free base of bisoprolol was blended, bleed was found and anchorage property and adhesion feeling were insufficient.

While the invention has been described in detail and with reference to specific embodiments thereof, it will be apparent to one skilled in the art that various changes and modifications can be made therein without departing from the spirit and scope thereof.

The present application is based on Japanese Patent Application No. 2005-358470 filed on Dec. 13, 2005 and Japanese Patent Application No. 2006-328922 filed on Dec. 6, 2006, and the contents are incorporated herein by reference.

Further, all references cited herein are incorporated in their entireties.

INDUSTRIAL APPLICABILITY

According to the adhesive pharmaceutical preparation of the invention, the compatibility of a polyisobutylene pressure-sensitive adhesive with a free base of bisoprolol can be specifically increased by containing a branched monoalcohol having from 12 to 28 carbon atoms as a solubilizing agent in the pressure-sensitive adhesive layer. As a result, not only it becomes possible to increase blending amount of bisoprolol but also bleed of bisoprolol from the pressure-sensitive adhesive layer can be suppressed and, what is more, the pressure-sensitive adhesion characteristics sufficient from the practical point of view can be obtained. Accordingly, an adhesive pharmaceutical preparation which can achieve compatibility of the pharmacological action with pressure-sensitive adhesion characteristics at high level can be provided.

The invention claimed is:

1. An adhesive pharmaceutical preparation containing bisoprolol, the preparation comprising:
   a backing; and
   a pressure-sensitive adhesive layer laminated on one side of the backing, said pressure-sensitive adhesive layer comprising at least one 2-alkyl-1-alkanol selected from the group consisting of 2-hexyl-1-decanol, 2-octyl-1-decanol, 2-hexyl-1-dodecanol, 2-octyl-1-dodecanol and 2-decyl-1-tetradecanol, a free base of bisoprolol, and a polyisobutylene pressure-sensitive adhesive comprising at least two species of polyisobutylene, wherein the first species of polyisobutylene has a viscosity average molecular weight of from 45,000 to 65,000 and the second species of polyisobutylene has a viscosity average molecular weight of from 4,000,000 to 5,000,000.

2. The preparation of claim 1, wherein the first species of polyisobutylene has a viscosity average molecular weight of 60,000 and the second species of polyisobutylene has a viscosity average molecular weight of 4,000,000.

3. The preparation of claim 2, wherein the pressure-sensitive adhesive layer comprises at least two species of 2-alkyl-1-alkanol, wherein the first species of 2-alkyl-1-alkanol is 2-octyl-1-decanol and the second species of 2-alkyl-1-alkanol is 2-hexyl-1-dodecanol.

4. The preparation of claim 1, wherein the pressure-sensitive adhesive layer further comprises an alicyclic saturated hydrocarbon resin having a softening point of 140° C.

5. The preparation of claim 2, wherein the pressure-sensitive adhesive layer further comprises an alicyclic saturated hydrocarbon resin having a softening point of 140° C.

6. The preparation of claim 3, wherein the pressure-sensitive adhesive layer further comprises an alicyclic saturated hydrocarbon resin having a softening point of 140° C.

7. The preparation of claim 1, wherein the pressure-sensitive adhesive layer further comprises isopropyl myristate.

8. The preparation of claim 2, wherein the pressure-sensitive adhesive layer further comprises isopropyl myristate.

9. The preparation of claim 3, wherein the pressure-sensitive adhesive layer further comprises isopropyl myristate.

10. The preparation of claim 4, wherein the pressure-sensitive adhesive layer further comprises isopropyl myristate.

11. The preparation of claim 5, wherein the pressure-sensitive adhesive layer further comprises isopropyl myristate.

12. The preparation of claim 6, wherein the pressure-sensitive adhesive layer further comprises isopropyl myristate.

* * * * *